United States Patent [19]
Kolin et al.

[11] Patent Number: 5,470,995
[45] Date of Patent: Nov. 28, 1995

[54] CONTINUOUS PROCESS FOR MAKING A DIALKYLTIN THIOCARBOXYLIC ACID ESTER

[75] Inventors: Kevin S. Kolin, Chicago, Ill.; Anthony J. Siegmann, Middletown, Ohio

[73] Assignee: Morton International, Inc., Chicago, Ill.

[21] Appl. No.: 278,769

[22] Filed: Jul. 22, 1994

Related U.S. Application Data

[63] Continuation-in-part of Ser. No. 259,604, Jun. 14, 1994, abandoned, which is a continuation of Ser. No. 84,381, Jun. 29, 1993, abandoned.

[51] Int. Cl.$^6$ .................................................. C07F 7/22
[52] U.S. Cl. ............................................ 556/91; 556/94
[58] Field of Search ........................................ 556/91, 94

[56] References Cited

U.S. PATENT DOCUMENTS

| | | | |
|---|---|---|---|
| 3,147,285 | 9/1964 | Mack | 260/348 |
| 3,293,273 | 12/1966 | Gloskey | 260/429.7 |
| 3,660,442 | 5/1972 | Ludwig | 260/429.7 |
| 4,237,043 | 12/1980 | Korbanka et al. | 260/45.75 S |
| 4,554,368 | 11/1985 | Maul et al. | 556/91 |

FOREIGN PATENT DOCUMENTS 1374024  11/1974  United Kingdom .

*Primary Examiner*—Porfirio Nazario-Gonzales
*Attorney, Agent, or Firm*—Robert M. Didrick; Gerald K. White

[57] ABSTRACT

This invention provides a method for reducing fifty-fold the size of equipment required for making a given volume of alkyltin thioglycolic acid esters. In said method, an alkyltin thiocarboxylic acid ester is made from the corresponding alkyltin halide and thiocarboxylic ester in a continuous process that requires but one agitated reaction vessel. The organic reactants and an acid acceptor are added simultaneously to a reaction vessel equipped with agitator impellers and containing a sufficient level of water to provide an agitatable medium. Extremely vigorous agitation (at least about 75, preferably at least about 90, turnovers per minute, which is sufficient to achieve a fluid velocity across the impeller(s) of at least about 50 feet per minute) is employed to avoid side reactions which often cause the formation of a tenacious, stringy emulsion, the breaking of which requires a rather difficult and wasteful filtration. Continuous withdrawal of the reaction mixture from said reactor is commenced promptly after commencement of the additions and said mixture is continuously separated into an aqueous phase and an organic phase as it is withdrawn without the need of demulsification means. The pH of the reaction mixture is greater than 7 but the maximum is about 8.2 and the temperature is from about 40 to about 80° C.

9 Claims, No Drawings

CONTINUOUS PROCESS FOR MAKING A DIALKYLTIN THIOCARBOXYLIC ACID ESTER

This is a continuation-in-part Ser. No. 08/259,604, filed on Jun. 14, 1994, now abandoned, which was a continuation of application Ser. NO. 08/084,381, filed Jun. 29, 1993, now abandoned.

BACKGROUND OF THE INVENTION

This invention relates to PVC stabilizers. In particular, it relates to a method for making an alkyltin thiocarboxylic acid ester from the corresponding alkyltin halide and thiocarboxylic ester. More particularly, it relates to a method for continuously synthesizing such an ester in an aqueous medium in a single vessel with extremely vigorous agitation.

Because of the drawbacks associated with the use of an organic solvent in batchwise preparations of such esters in the past (e.g., diminished yields based on the space and time allotted to the process), some have turned to methods in which the product is still made batchwise but with the elimination of the organic solvent. These, too, have their shortcomings. If the reaction mixture is strongly alkaline at the beginning of a batch, the pH decreases only gradually as the alkyltin halide is introduced; such conditions favor the hydrolysis of the starting materials. To minimize such hydrolysis, low temperatures are necessary during the rather long holding times associated with batchwise procedures. Side reactions such as the formation of alkyltin oxide by the reaction of ammonium hydroxide (an acid acceptor) and the alkyltin halide, and the base-catalyzed hydrolysis of the thiocarboxylic ester cause loss of desired product and produce materials which often cause the formation of a tenacious, stringy emulsion, the breaking of which requires a rather difficult and wasteful filtration.

Maul et al (U.S. Pat. No. 4,554,368) proposes to provide a continuous process for the preparation of these esters which comprises carrying out the reaction continuously in a system consisting of 1 to 5 agitated vessels with an average dwell time of 1 to 60 minutes at a constant pH value in the range from 3 to 8 and at a temperature from 40° to 80° C. Maul teaches that it is convenient to initiate the reaction batchwise, pumping the alkyltin chloride and the thiocarboxylic acid ester in the required molar ratio into the first reactor to fill it halfway before an aqueous solution of the base is added with stirring to raise the pH to the desired value. Then, the continuous addition of base, ester, and chloride is started and the volume of the reaction mixture is controlled by pumping it into a second agitator vessel. It is not clear that the continuous process described by Maul in terms of two agitator vessels would be successful when only one agitator vessel is used.

There remains a need, therefore, for a continuous process for the preparation of alkyltin thioglycolic acid esters from the corresponding halides and esters in an aqueous medium which produces a two phase product mixture which is substantially instantaneously separable in the absence of demulsification means.

There remains a further need for a process for the preparation of alkyltin thioglycolic acid esters from the corresponding halides and esters which is continuous from the start for an indefinitely long period wherein the use of but one agitator vessel for the reaction dramatically increases the yield of product on the basis of the reactor volume employed and the time expended for the process.

SUMMARY OF THE INVENTION

It is an object of this invention, therefore, to provide a continuous process for the manufacture of alkyltin thioglycolic acid esters that requires but one agitated reactor.

It is another of this invention to provide a method for preparing an alkyltin thiocarboxylic acid ester in a single vessel wherein an aqueous/organic reaction mixture is continuously formed and vigorously agitated while a portion of said mixture is continuously withdrawn and quickly separated into two phases—the product and an aqueous solution of an inorganic halide—in the absence of demulsification means.

It is a further object of this invention to provide a method for the preparation in an aqueous medium of such an ester wherein the alkyltin halide, thiocarboxylic acid ester, and acid acceptor are simultaneously added to a single reactor and the resulting reaction mixture is stirred vigorously at a constantly alkaline pH value.

It is a related object of this invention to provide a method for reducing fifty-fold the size of equipment required for making a given volume of alkyltin thioglycolic acid esters.

These and other objects of the invention which will become apparent from the following description are achieved by simultaneously adding an alkyltin halide, a thiocarboxylic acid ester, and an acid acceptor to an agitated reactor continuously over an indefinite period of time, maintaining the resulting reaction mixture at a pH of from greater than 7 to about 8.2, agitating the mixture with one or more impellers at a rate of at least about 75 turnovers per minute, which is sufficient to achieve a fluid velocity across the impeller(s) of at least about 50 feet per minute, but preferably at least about 90 turnovers per minute when the residence time is 5 minutes or more and at least about 110 turnovers per minute at a residence time of from 3.6 minutes to 5 minutes, with the proviso that two or more impellers are spaced apart sufficiently to maintain said fluid velocity substantially throughout the operating volume, continuously withdrawing the mixture from said reactor, and continuously separating it as it is withdrawn into an aqueous phase and an organic phase without the benefit of a demulsification means. In this context, substantially throughout means entirely throughout or so close to it that the difference is not meaningful.

DETAILED DESCRIPTION OF THE PREFERRED EMBODIMENTS

The alkyltin thiocarboxylic ester has the structure:

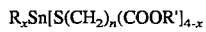

$$R_xSn[S(CH_2)_n(COOR')]_{4-x}$$

wherein x is 1 or 2, and n is 1 or 2; R is a alkyl group having from one to four carbon atoms); and R' is an alkyl group having from eight to sixteen carbon atoms. The source of the R group is the lower-alkyltin halide as it reacts with the HS- group of the thiocarboxylic ester bearing the R' group. As used herein, the word halide means chloride or bromide. An alkyltin chloride is preferred. The halide is suitably a mixture of mono- and di-alkyl compounds which are accordingly the tri- or di-halide. A suitable ratio of the dialkyl to mono-alkyl groups in a mixture is from about 10:1 to about 1:10 by weight, preferably from about 5:1 to about 3:1, more preferably about 4:1. R is preferably methyl or butyl and more preferably methyl. R' is exemplified by n-octyl, iso-octyl, 2-ethylhexyl, tridecyl, and hexadecyl radicals. Examples of the alkyltin halides include monomethyltin trichloride, dimethyltin dichloride, mixtures thereof, monobutyltin trichloride, dibutyltin dichloride, and mixtures thereof. The thiocarboxylic acid esters are exemplified by 2-ethylhexylthioglycolate, isooctyl thioglycolate, 2-ethylhexylmercaptopropionate, and mixtures of such esters. The alkyltin halides and the thiocarboxylic acid esters are hereinafter referred sometimes to as organic reactants as opposed to the acid acceptor reactant.

The acid acceptor is preferably ammonium hydroxide but any of the conventionally used alkaline materials such as sodium hydroxide, potassium hydroxide, sodium carbonate, and a watersoluble amine is suitable.

The alkyltin halide is added as a water solution which is suitably about 50% water by weight. It is preferable to charge the reactor with an amount of water equal to about 80% of the reactor volume before the addition of the reactants is commenced in order to provide an agitatable reaction medium at the outset. The simultaneous addition of the organic reactants and the acid acceptor is controlled by a computer programmed to set an initial set of addition rates and to change those rates as data from the reaction mixture is fed into the computer. The rate of addition of each organic reactant is determined by the stoichiometry of the reaction as it applies to the equivalent weights, the purity, and the concentration of each. In the special case of alkyltin halide mixtures, the ratio of di- and tri-halides and the consequent effective equivalent weight of the mixture is a determinant. The pH of the reaction mixture is also fed constantly into the computer so that the rate of addition of the acid acceptor reactant may be controlled to keep the reaction going at a substantially constant alkaline pH, preferably from about 8 to about 8.2. The simultaneous addition is suitably achieved by feeding each organic reactant through a separate tube extending below the surface of the liquid in the reactor to the level of the uppermost impeller. Said reactants may be fed through the inner and outer components of a coaxial tube.

Agitation of the mixture is suitably accomplished with a center-mounted LIGHTNIN Series XDQ, Model XDQ-75SCR mixer equipped with one or more A310 laser foil impellers. Said mixer has a 0.75 HP, variable speed (1750 RPM max), DC motor. Other mixers having similar capabilities are also suitable. The diameter of the impellers is selected as appropriate to the size and the design of the particular reactor vessel used, as exemplified hereinbelow.

The turnover rate (the statistical number of times per minute that a point within the liquid moves to the surface) is calculated by dividing the primary flow of the reaction mixture, which is also known as the pumping rate of the impellers in the system, by the operating volume. The speed of the impellers is, of course, only one of many factors determining the turnover rate. For example, a pair of 2.5 inch LIGHTNIN A310 laser foil impellers spaced apart 4 inches on a mixer shaft turning at 1200 RPM in a reaction mixture 8 inches deep in a baffled cylindrical vessel having a diameter of 5 inches caused a turnover rate of 120, and a pair of 5.2 inch A310 impellers spaced apart 4 inches on a mixer shaft turning at 1200 RPM in a reaction mixture 12 inches deep in a baffled cylindrical vessel having an 11.5 inch diameter caused a turnover rate of 128. The fluid velocity across the impellers is calculated by dividing the pumping rate of the impellers by the cross sectional area of the reactor. In the smaller system described above, the fluid velocity across the impellers is 81 feet per minute whereas it is 129 feet per minute at the same impeller speed in the larger system. A preferred mixer speed for the smaller system is from about 1100 RPM to about 1300 RPM.

An article entitled "Let's Understand Mixing" by Dr. James Y. Oldshue and published by Mixing Equipment Co., Inc. is hereby incorporated by reference for its discussion of the key mixing parameters and of the effect on other design variables when one parameter is held constant during scale-up calculations.

Preferably, the agitation speed is such that the turnover rate is at least about 120. Although there is no maximum speed except for the practical limitations placed on the speed by the mountings for the mixer, the need to avoid excessive vibrations, and the economy of using no more mixing energy than is necessary, the turnover rate is preferably no more than about 200. At these preferred turnover rates, the fluid velocity across the impeller(s) is at least about 80 feet/minute. When there is more than one impeller on the shaft of the mixer, the spacing between them is adjusted so that the turnover rate will be substantially uniform throughout the operating volume of the reaction mixture. The Z-factor or ratio of the liquid depth to the diameter of the reactor vessel is used by those of ordinary skill in the art of mixing to determine whether a second impeller is needed and what the spacing should be.

The reaction mixture is continuously drawn off at the bottom of the vessel through an overflow leg at the same rate as the total of the additions. Thus, the withdrawal of the reaction mixture from the stirred vessel is commenced promptly (i.e., within 30 seconds) after the start of the simultaneous additions and the commencement of the withdrawals is nearly simultaneous with the commencement of the additions. The residence time for the reaction mixture in the stirred vessel is suitably within the range of from about 2 minutes to about 6 minutes, but it is preferably 3.6 minutes or more. The mixture is then piped continuously into a separation unit wherein the separation of the aqueous phase is continuous and essentially instantaneous without the need of filtration or any other demulsification means. A gravity settling separation tank and a liquid/liquid centrifugal separator are both suitable. The continuous stream of the organic phase is preferably washed with fresh water and then flash dried with heat and vacuum before being clarified by filtration. Finally, the clear product is piped into a storage tank or directly into machines for filling shipping containers. The wash water may be recycled into the reactor as part of the continuous make-up of the reaction mixture.

The operating temperature of the reaction mixture is preferably about 50° C. but because the pH is maintained between 7 and 8.2 excursions into the 75°–80° C. range are not harmful. A temperature of from about 40° to about 50° C. is suitable if one wishes to absorb the heat of reaction with cooling water; a temperature of about 55–60 may be maintained by the adiabatic operation of the method. As a practical matter, the maintenance of the pH between 7 and 8 is extremely difficult because of the wide swings of a pH meter between those values during the addition of reactants and acid acceptor. Therefore, it is much preferred to maintain the pH at about 8–8.2. It will be appreciated by those of ordinary skill in the art that although the addition of the acid acceptor is made at the same time as the additions of the organic reactants, it will not necessarily be a continuous addition. The constraints of maintaining a substantially constant pH may make it necessary to temporarily halt the addition of the acid acceptor while the addition of the organic reactants continues. The concentration of the aqueous solution of acid acceptor may be adjusted so that the computer controlling the addition may direct a continuous stream of the solution into the stirred reactor. The computer program controlling the additions is written in Microsoft Basic language, using subroutines purchased as part of an A to D converter from Keithley Instruments of Cleveland, Ohio. With this program, the computer calculates a control signal between 0 and 100% and writes it to the A to D converter which sends the signal to an I & P converter, thence to the control device. In summary the program handles the following tasks:

Charging calculations for the ester and organotin halide solution;
Operator interface screens;
Ester mass flow rate control;
Organotin halide solution mass flow rate control;
pH control;
Fresh water flow control;
Reactor temperature control;
Separation column level control;
Wash column level control;
Temperature monitoring;
Real time graphs;
Data storage; and
Start-up and shut-down control.

```
KEY OFF:CLS:DCT=0
SIG=0:X=40:SHUT=0
DIM TIME%(6),RTIME%(6),RUNTIME%(6),OLDRUNTIME%(6)
DIM A(8),B(8),C(8),D(8),TV(15),TLABEL$(50)
DIM VARI$(50),VALUE(50),GNAME$(50),GV(50),CV(50)
DATA 18,34.43,67.48,54.77
DATA 19,34.55,67.12,54.53
DATA 20,34.67,66.77,54.29
DATA 21,34.79,66.41,54.06
DATA 22,34.91,66.06,53.82
DATA 23,35.03,65.71,53.59
DATA 24,35.15,65.37,53.36
DATA 25,35.27,65.02,53.14
DATA TSP,TOSP,ASP,WSP,TEMPSP,KPH1
DATA PHSP,KLEVEL,KWASH,SHUT DOWN,START UP
DATA TIN FLOW,ESTER FLOW,AMMONIA FLOW,WATER FLOW
DATA REACTOR pH,SEPS LEVEL,CANCEL GRAPH
DATA REACTOR TEMP,WASH TEMP,PREHEAT TEMP,FILM TEMP
DATA DISTILATE VAPOR TEMP,PRODUCT TEMP,WATER DIST IN
DATA WATER DIST OUT,STEAM TEMP,WATER PRODUCT OUT,MALOTT
DATA BEGIN TAKING SAMPLE,END TAKING SAMPLE,SHUT DOWN,START UP
DATA INPUT COMMENT,CANCEL COMMENT,HALF LIFE
DATA MANUAL SEP,AUTOMATIC SEP,MANUAL WASH,AUTOMATIC WASH
DATA ALL MANUAL,ALL AUTOMATIC,CANCEL,HALF LIFE
FOR I=1 TO 8
    READ A(I),B(I),C(I),D(I)
NEXT I
FOR I=1 TO 50
    READ VARI$(I)
    IF VARI$(I)="START UP" THEN I=50
NEXT I
FOR I=1 TO 50
    READ GNAME$(I)
    IF GNAME$(I)="CANCEL GRAPH" THEN I=50
NEXT I
FOR I=0 TO 50
    READ TLABEL$(I)
    IF TLABEL$(I)="MALOTT" THEN I=50
  NEXT I
FOR I=1 TO 50
    READ COMMENT$(I)
    IF COMMENT$(I)="HALF LIFE" THEN I=50
NEXT I
FOR M=1 TO 50
    READ MANUAL$(M)
    IF MANUAL$(M)="HALF LIFE" THEN M=50
NEXT M

CLS:SCREEN 2:ON ERROR GOTO 1500
PRINT "                TM181-EH CHARGING CALCULATION
PRINT
LOCATE 6,1
INPUT "LBS TO26 USING ###.##:";TOSP
INPUT "PERCENT MONO NEAT USING ##.#:";MN
INPUT "PERCENT CHLORINE USING ##.##:";CH
INPUT "DESIRED TIN IN PRODUCT USING ##.#:";TIN
FOR I=1 TO 8
    IF MN<A(I) THEN 50
NEXT I
```

```
M=I:SP=TOSP
PCL=B(M)-(A(M)-MN)*(B(M)-B(M-1))/(A(M)-A(M-1))
RXSN=C(M)-(A(M)-MN)*(C(M)-C(M-1))/(A(M)-A(M-1))
WTSN=D(M)-(A(M)-MN)*(D(M)-D(M-1))/(A(M)-A(M-1))
CON=CH/PCL*100
B=CON*((MN*.4944)+(100-MN)*.5403)/10000
C=(CON-CH-(CH/35.453))/100
D=TIN
TSP=TOSP*D/100/(B-C*D/100)
LOCATE 15,1:PRINT "LBS OF DMTDCL TO CHARGE:"
LOCATE 15,26:PRINT USING "###.##";TSP
ASP=TSP*CH*17/35.454/100/.28
LOCATE 16,1:PRINT "LBS OF AQ AMMONIA TO CHARGE:"
LOCATE 16,29:PRINT USING "###.##";ASP
EQCHL=TSP*CH/35.454/100
THEORY=TOSP-EQCHL+RXSN*EQCHL
LOCATE 17,1:PRINT "THEORY YIELD:"
LOCATE 17,15:PRINT USING "###.##";THEORY
PSN=WTSN*EQCHL/THEORY*100
WSP=TOSP*1.1/2
CALL SOFTINIT
CALL INIT

'******************
'    Start Time
'******************
CALL CLOCKREAD(TIME%(),"NT","")
FOR J=0 TO 2
    RTIME%(J)=TIME%(J)
NEXT J
LOCATE 22,1:INPUT "DO YOU WISH TO START PROCESS:";Q$
IF Q$="Y" OR Q$="y" GOTO 100
GOTO 10
LOCATE 23,1:INPUT "DO YOU WISH TO SAVE DATA:";Q$
IF Q$="Y" OR Q$="y" THEN
    DCT=1
END IF:GOTO 101
CLS:COLOR 2,7:LOCATE 10,10:PRINT "THIS PROGRAM IS THE MASTERPIECE"
LOCATE 13,11:PRINT "OF K.S.K. AND REVISED BY C.B.B."
IF INKEY$="" THEN 600

'********************
'      SCREEN
'********************
SCREEN 9,0
LINE(0,0)-(0,330),1:LINE(620,0)-(620,330),1
LINE(0,0)-(620,0),1:LINE(0,330)-(620,330),1
LINE(5,5)-(615,5)
LINE(5,115)-(5,5)
LINE(615,5)-(615,115)
LINE(5,115)-(615,115)
LINE(10,10)-(610,10),1
LINE(10,10)-(10,110),1
LINE(10,110)-(610,110),1
LINE(610,10)-(610,110),1
LINE(200,10)-(200,110),1
LINE(400,10)-(400,110),1
LINE(10,30)-(610,30),1
LOCATE 2,8:PRINT "TIN FLOW"
```

```
LOCATE 4,5:PRINT "SET POINT: "
LOCATE 5,5:PRINT "ACTUAL FLOW: "
LOCATE 7,5:PRINT "% VALVE OPEN: "
LOCATE 2,33:PRINT "TO-26 FLOW"
LOCATE 4,30:PRINT "SET POINT: "
LOCATE 5,30:PRINT "ACTUAL FLOW: "
LOCATE 7,30:PRINT "% VALVE OPEN: "
LOCATE 2,58:PRINT "AMMONIA FLOW"
LOCATE 4,55:PRINT "SET POINT: "
LOCATE 5,55:PRINT "ACTUAL FLOW: "
LOCATE 7,55:PRINT "% VALVE OPEN: "
LOCATE 6,55:PRINT "pH: "
LINE(610,125)-(610,180),3
LINE(380,125)-(380,180),3
LINE(380,125)-(610,125),3
LINE(380,180)-(610,180),3
LOCATE 10,50:PRINT "ACTUAL TIME: "
LOCATE 12,50:PRINT "RUNNING TIME: "
LINE(10,125)-(10,325),4
LINE(10,123)-(180,123),4
LINE(10,325)-(180,325),4
LINE(180,325)-(180,125),4
LINE(185,123)-(350,123),4
LINE(185,125)-(185,325),4
LINE(185,325)-(350,325),4
LINE(350,325)-(350,125),4
LINE(10,221)-(180,221),4
LINE(10,140)-(180,140),4
LINE(185,140)-(350,140),4
LINE(10,238)-(180,238),4
LINE(185,193)-(350,193),4
LINE(185,211)-(350,211),4
LINE(185,263)-(350,263),4
LINE(185,281)-(350,281),4
LOCATE 10,25:PRINT "INITIAL SEPARATIONS"
LOCATE 10,6:PRINT "MAKE-UP WATER"
LOCATE 17,5:PRINT "COOLING WATER"
LOCATE 12,4:PRINT "SET POINT: "
LOCATE 13,4:PRINT "ACTUAL FLOW: "
LOCATE 15,4:PRINT "% VALVE OPEN: "
LOCATE 22,4:PRINT "% VALVE OPEN: "
LOCATE 20,4:PRINT "ACTUAL TEMP: "
LOCATE 19,4:PRINT "TEMP SET PT: "
LOCATE 12,25:PRINT "PRODUCT HT: "
LOCATE 13,25:PRINT "% VALVE OPEN: "
LOCATE 15,29:PRINT "WASH COLUMN"
LOCATE 20,27:PRINT "TO-26 EXTRACTION"
LOCATE 17,25:PRINT "PRODUCT HT:"
LOCATE 18,25:PRINT "% VALVE OPEN:"
LOCATE 22,25:PRINT "PRODUCT HT:"
LOCATE 23,25:PRINT "% VALVE OPEN:"
IF SIG=25 THEN 105
SIG=25

'***************************
'     CONTROL PROGRAM
'***************************
CALL IONMANA("TIN",5,13,12,1,-1)
CALL IONMANA("TO26",5,10,12,1,-1)
CALL IONMANA("AMMONIA",5,11,12,1,-1)
```

```
CALL IONMANA("WATER",5,14,12,1,-1)
CALL IONMANA("ALARM",5,9,12,1,-1)
CALL IONMANA("COLDJUNC",3,32,12,1,-1)
CALL IONMANA("TEMP",3,0,12,1,-1)
CALL IONMANA("TEMP1",3,1,12,1,-1)
CALL IONMANA("TEMP2",3,2,12,1,-1)
CALL IONMANA("TEMP3",3,3,12,1,-1)
CALL IONMANA("TEMP4",3,4,12,1,-1)
CALL IONMANA("TEMP5",3,5,12,1,-1)
CALL IONMANA("TEMP6",3,6,12,1,-1)
CALL IONMANA("TEMP7",3,7,12,1,-1)
CALL IONMANA("TEMP8",3,8,12,1,-1)
CALL IONMANA("TEMP9",3,9,12,1,-1)
CALL IONMANA("PH",5,15,12,1,-1)
CALL IONMANA("SEP",6,12,12,1,-1)
CALL IONMANA("WASH",6,14,12,1,-1)
CALL IONMANA("TINOUT",8,2,-1,-1,-1)
CALL IONMANA("TOOUT",8,1,-1,-1,-1)
CALL IONMANA("AMMONIAOUT",8,3,-1,-1,-1)
CALL IONMANA("WATEROUT",8,0,-1,-1,-1)
CALL IONMANA("COOLOUT",9,3,-1,-1,-1)
CALL IONMANA("SEPOUT",9,2,-1,-1,-1)
CALL IONMANA("WASHOUT",9,0,-1,-1,-1)

CALL ANIN("TINFEED%",5.0,"TIN",1,-1,"NT","")
CALL ANIN("TOFEED%",5.0,"TO26",1,-1,"NT","")
CALL ANIN("AMMFEED%",5.0,"AMMONIA",1,-1,"NT","")
CALL ANIN("WATERFEED%",5.0,"WATER",1,-1,"NT","")
CALL ANIN("TEMPIN%",1.0,"COLDJUNC,TEMP,TEMP1,TEMP2,TEMP3",1,-1,"NT","")
CALL ANIN("TEMPIN2%",1.0,"COLDJUNC,TEMP4,TEMP5,TEMP6",1,-1,"NT","")
CALL ANIN("TEMPIN3%",1.0,"COLDJUNC,TEMP7,TEMP8,TEMP9",1,-1,"NT","")
CALL ANIN("PHIN%",5.0,"PH",1,-1,"NT","")
CALL ANIN("SEPIN%",15.0,"SEP",1,-1,"NT","")
CALL ANIN("WASHIN%",5.0,"WASH",1,-1,"NT","")
CALL ANIN("ALARM%",5.0,"ALARM",1,-1,"NT","")

'****************
'    Variables
'****************
TK1=150:TVA!=0
TOK1=160:TOVA!=0
AK1=120:AVA!=0
WK1=50:WVA!=0
T=1:TI=3:TD=.75
TOT=1:TOTI=40:TOTD=.5
WK1=50:WT=2.5: WTI=1000000:WTD=0
TEMPSP=55:TEMPK1=20
KPH1=.15:PHSP=8.2
KLEVEL=18:LEVELSP=6:TSI=120:TSD=30
KWASH=10:SEPVAR=1900:WASHVAR=3900

CALL INTON(1,"MIL")
'****************
'    Tin Flow
'****************
CALL MEANDEV("TINFEED%",1,GV(1),STDEV!,1.0,5.0,0)
 CV(1)=INT((.6661*GV(1)-1.2715)*100+.5)/100
IF CV(1)<0 THEN CV(1)=0
ERR1=TSP-CV(1)
DTVA=TK1*((1+T/TI+TD/T)*ERR1-(1+2*TD/T)*ERR2+TD/T*ERR3)
```

```
TVA!=TVA!+TK1*ERR1
ERR3=ERR2:ERR2=ERR1
IF TVA!<0 THEN TVA!=0
IF TVA!>3900 THEN TVA!=3900
PERT=(TVA!/3900)*100

'***************
'   to26 flow
'***************
CALL MEANDEV("TOFEED%",1,GV(2),STDEV!,1.0,5.0,0)
CV(2)=INT((.678*GV(2)-1.27)*100+.5)/100
IF CV(2)<0 THEN CV(2)=0
TERR1=TOSP-CV(2)
TOVA!=TOVA!+TOK1*TERR1
TERR3=TERR2:TERR2=TERR1
IF TOVA!<0 THEN TOVA!=0
IF TOVA!>3900 THEN TOVA!=3900
PERTO=(TOVA!/3900)*100

'*******************
'   Ammonia Flow
'*******************
CALL INTOFF
CALL MEANDEV("AMMFEED%",1,GV(3),STDEV!,1.0,5.0,0)
CV(3)=INT((.6679*GV(3)-1.2673)*100+.5)/100
IF CV(3)<0 THEN CV(3)=0

CALL MEANDEV("PHIN%",1,GV(5),STDEV!,1.0,5.0,0)
CV(5)=INT((1.8786*GV(5)-3.563)*100+.5)/100
PHERR=PHSP-CV(5)
ASP=ASP+KPH1*PHERR
IF ASP<0 THEN ASP=0
IF ASP>2.5 THEN ASP=2.5
AERR1=ASP-CV(3)
AVA!=AVA!+AK1*AERR1
IF AVA!<0 THEN AVA!=0
IF AVA!>3900 THEN AVA!=3900
PERAMM=(AVA!/3900)*100
AERR3=AERR2:AERR2=AERR1

'***********************
'   Make-up Water Flow
'***********************
CALL MEANDEV("WATERFEED%",1,GV(4),STDEV!,1.0,5.0,0)
CV(4)=INT((3.7721*GV(4)-7.2120)*100+.5)/100*60/454
IF CV(4)<0 THEN CV(4)=0
WERR1=WSP-CV(4)
WVA!=WVA!-WK1*WERR1
IF WVA!<0 THEN WVA!=0
IF WVA!>3900 THEN WVA!=3900
PERW=(1-WVA!/3900)*100

'******************************
'   Reactor Cooling Water Flow
'******************************
CALL ARGETVALF("TEMPIN%",1.0,2,"TEMP",TV(0),10)
TEMPERR=TEMPSP-TV(0)
TEMPCNTRL!=TEMPCNTRL!+TEMPERR*TEMPK1
IF TEMPCNTRL!<0 THEN TEMPCNTRL!=0
IF TEMPCNTRL!>3900 THEN TEMPCNTRL!=3900
```

```
PERTEMP=(1-TEMPCNTRL!/3900)*100

'****************************
' Sep Column Level Control
'****************************
IF SEP=1 THEN 1600
CALL MEANDEV("SEPIN%",1,GV(6),STDEV,1.0,15.0,0)
CV(6)=GV(6)
IF GV(6)<.80 THEN GV(6)=0
LVLER=LEVELSP-CV(6)
DLC=KLEVEL*(LVLER+TSD*(LVLER-LVLER1))
LEVELCNTRL!=LEVELCNTRL!+DLC
LVLER2=LVLER1
LVLER1=LVLER
IF LEVELCNTRL!<0 THEN LEVELCNTRL!=0
IF LEVELCNTRL!>SEPVAR THEN LEVELCNTRL!=SEPVAR
PERLEVEL=LEVELCNTRL!/3900*100

'****************************
' Wash Column Level Control
'****************************
IF WAS=1 THEN 1700
CALL MEANDEV("WASHIN%",1,GV(7),STDEV,1.0,5.0,0)
CV(7)=GV(7)
IF GV(7)<.88 THEN GV(7)=0
WASHER=WASHSP-GV(7)
WASHCNTRL!=WASHCNTRL!+KWASH*WASHER
IF WASHCNTRL!<0 THEN WASHCNTRL!=0
IF WASHCNTRL!>3900 THEN WASHCNTRL!=3900
PERWASH=WASHCNTRL!/3900*100

'*********************************************
'    falling film temperature profiles
'*********************************************
CALL ARGETVALF("TEMPIN%",1.0,3,"TEMP1",TV(1),10)
CALL ARGETVALF("TEMPIN%",1.0,4,"TEMP2",TV(2),10)
CALL ARGETVALF("TEMPIN%",1.0,5,"TEMP3",TV(3),10)
CALL ARGETVALF("TEMPIN2%",1.0,2,"TEMP4",TV(4),10)
CALL ARGETVALF("TEMPIN2%",1.0,3,"TEMP5",TV(5),10)
CALL ARGETVALF("TEMPIN2%",1.0,4,"TEMP6",TV(6),10)
CALL ARGETVALF("TEMPIN3%",1.0,2,"TEMP7",TV(7),10)
CALL ARGETVALF("TEMPIN3%",1.0,3,"TEMP8",TV(8),10)
CALL ARGETVALF("TEMPIN3%",1.0,4,"TEMP9",TV(9),10)

'**********************
'   distillate alarm
'**********************
CALL ARGETVALF("ALARM%",5.0,1,"ALARM",ALARM,0)
LOCATE 18,50:PRINT "                    "
IF ALARM<4 THEN
    LOCATE 18,50
    PRINT "EMPTY DISTILLATE"
END IF '**************************
'     Indicators
'**************************
IF SHUT=1 THEN
    LOCATE 21,50:PRINT "SHUT DOWN SEQUENCE"
    LOCATE 22,50:PRINT "    INITIATED"
```

```
END IF
IF SEP=1 THEN
    LOCATE 15,50:PRINT "MANUAL SEP CONTROL"
END IF
IF WAS=1 THEN
    LOCATE 16,50:PRINT "MANUAL WASH CONTROL"
END IF

CALL WRITEVAR("TINOUT",2,TVA!,-1,"NT")
CALL WRITEVAR("TOOUT",2,TOVA!,-1,"NT")
CALL WRITEVAR("AMMONIAOUT",2,AVA!,-1,"NT")
CALL WRITEVAR("WATEROUT",2,WVA!,-1,"NT")
CALL WRITEVAR("COOLOUT",2,TEMPCNTRL!,-1,"NT")
CALL WRITEVAR("SEPOUT",2,LEVELCNTRL!,-1,"NT")
CALL WRITEVAR("WASHOUT",2,WASHCNTRL!,-1,"NT")

IF TRIP=30 THEN 700
TRIP=TRIP+1
IF TON=1 THEN 1110
IF GON=1 THEN 1000

LOCATE 4,16:PRINT USING "##.##";TSP
LOCATE 5,18:PRINT USING "##.##";CV(1)
LOCATE 7,19:PRINT USING "###";PERT
LOCATE 4,41:PRINT USING "##.##";TOSP
LOCATE 5,43:PRINT USING "##.##";CV(2)
LOCATE 7,44:PRINT USING "###";PERTO
LOCATE 4,66:PRINT USING "##.##";ASP
LOCATE 5,68:PRINT USING "##.##";CV(3)
LOCATE 7,69:PRINT USING "###";PERAMM
LOCATE 12,15:PRINT USING "##.#";WSP
LOCATE 13,17:PRINT USING "##.##";CV(4)
LOCATE 15,18:PRINT USING "###";PERW
LOCATE 6,58:PRINT USING "##.##";CV(5)
LOCATE 19,18:PRINT USING "##.#";TEMPSP
LOCATE 20,18:PRINT USING "##.#";TV(0)
LOCATE 22,18:PRINT USING "###";PERTEMP
LOCATE 12,37:PRINT USING "##.##";GV(6)
LOCATE 13,39:PRINT USING "###";PERLEVEL
LOCATE 17,37:PRINT USING "##.##";GV(7)
LOCATE 18,39:PRINT USING "###";PERWASH

'******************
'   NEW VARIABLE
'******************
A$=INKEY$
IF A$="T" OR A$="t" THEN 1100
IF A$="M" OR A$="m" THEN 1800
IF A$="G" OR A$="g" THEN 900
IF A$="X" OR A$="x" THEN 103
IF A$="C" OR A$="c" THEN 1200
IF A$=" " THEN 110
C$=INKEY$
IF C$=" " THEN 600

'******************
'       CLOCK
'******************
CALL CLOCKREAD(TIME%(),"NT","")
IF GON=0 THEN
```

```
    FOR J=0 TO 2
        LOCATE 10,J*3+65:PRINT USING "##";TIME%(J)
        RUNTIME%(J)=TIME%(J)-RTIME%(J)
    NEXT J

RT2=RUNTIME%(0)*3600+RUNTIME%(1)*60+RUNTIME%(2)
    RUNTIME%(0)=INT(RT2/3600)
    RUNTIME%(1)=INT(RT2/60-RUNTIME%(0)*60)
    RUNTIME%(2)=INT(RT2-RUNTIME%(0)*3600-RUNTIME%(1)*60)

FOR J=0 TO 2
        LOCATE 12,J*3+65:PRINT USING "##";RUNTIME%(J)
    NEXT J
END IF
GOTO 105

'**************************
'       Variable List
'**************************
CLS:LOCATE 2,26:PRINT "CONTROL VARIABLE LIST"
LOCATE 3,26:PRINT "-------- -------- ----"
LOCATE 5,8:PRINT "NUMBER":LOCATE 6,8:PRINT "------"
LOCATE 4,20:PRINT "VARIABLE":LOCATE 5,22:PRINT "NAME"
LOCATE 6,20:PRINT "--------"
LOCATE 4,35:PRINT "CURRENT":LOCATE 5,36:PRINT "VALUE"
LOCATE 6,35:PRINT "-------"
VALUE(1)=TSP
VALUE(2)=TOSP
VALUE(3)=ASP
VALUE(4)=WSP
VALUE(5)=TEMPSP
VALUE(6)=KPH1
VALUE(7)=PHSP
VALUE(8)=KLEVEL
VALUE(9)=KWASH
FOR I=1 TO 50
    LOCATE I+6,10:PRINT I
    LOCATE I+6,20:PRINT VARIS(I)
    LOCATE I+6,35:PRINT USING "####.##";VALUE(I)
    IF VARIS(I)="START UP" THEN I=50
NEXT I
ON ERROR GOTO 1500
LOCATE 23,10:INPUT "ENTER NUMBER OF VARIABLE YOU WISH TO CHANGE:";NV
IF VARIS(NV)="" THEN 600
IF VARIS(NV)="SCREEN" THEN
    CLS
    GON=0:TON=0
    X=40
    GOTO 101
END IF
IF VARIS(NV)="SHUT DOWN" THEN 1300
IF VARIS(NV)="START UP" THEN 1400
LOCATE NV+6,35:INPUT VALUE(NV)
TSP=VALUE(1)
TOSP=VALUE(2)
ASP=VALUE(3)
WSP=VALUE(4)
TEMPSP=VALUE(5)
KPH1=VALUE(6)
PHSP=VALUE(7)
```

```
KLEVEL=VALUE(8)
KWASH=VALUE(9)
GOTO 600

'*********************
'      Data Files
'*********************
IF DCT=0 THEN 710
OPEN "C:TIME.PRN" FOR APPEND AS #1
PRINT #1,TIME%(0),TIME%(1),TIME%(2)
CLOSE #1
OPEN "C:FLOW.PRN" FOR APPEND AS #2
PRINT #2,CV(1),CV(2),CV(3),CV(4),CV(5),CV(6),CV(7)
CLOSE #2
OPEN "C:TEMP.PRN" FOR APPEND AS #3
PRINT #3,TV(0),TV(1),TV(2),TV(3),TV(4),TV(5),TV(6),TV(7),TV(8),TV(9)
CLOSE #3
OPEN "C:COMMENT.PRN" FOR APPEND AS #4
PRINT #4,CMMT$
CLOSE #4
CMMT$=""
TRIP=0:GOTO 115

'***********************
'      Graph Section
'***********************
CLS:LOCATE 2,26:PRINT "VARIABLE GRAPHING LIST"
LOCATE 3,26:PRINT "-------- -------- ----"
LOCATE 5,8:PRINT "NUMBER":LOCATE 6,8:PRINT "------"
LOCATE 4,20:PRINT "VARIABLE":LOCATE 5,22:PRINT "NAME"
LOCATE 6,20:PRINT "--------":LOCATE 6,22:PRINT "----"

FOR I=1 TO 50
    LOCATE I+6,10:PRINT I
    LOCATE I+6,20:PRINT GNAMES(I)
    IF GNAMES(I)="CANCEL GRAPH" THEN I=50
NEXT I
LOCATE 23,10:INPUT "ENTER NUMBER OF VARIABLE YOU WISH TO GRAPH:";NV
IF GNAMES(NV)="CANCEL GRAPH" THEN
    GON=0
    GOTO 600
END IF
GON=1:TON=0:CLS
LINE(40,0)-(40,310)
LINE(40,310)-(600,310)
LOCATE 24,30:PRINT "TIME"
LOCATE 2,60:PRINT GNAMES(NV)
LOCATE 3,60:PRINT CV(NV)
Y=-34.44*GV(NV)+344.4
IF X=40 THEN 1010
LINE(X,Y)-(X-1,YOLD)
YOLD=Y:X=X+1
IF X=600 THEN
    X=40
    GOTO 990
END IF
GOTO 120

'*****************************
'      Temperature Profiles
```

```
'***********************
CLS:TON=1:GON=1
LOCATE 2,13:PRINT "PALLETIZABLE INTERNATIONAL TIN STABILIZER SYSTEM"
LOCATE 3,13:PRINT "--------------- --------------- --- ----------- ------"
LOCATE 5,24:PRINT "FFFE TEMPERATURE PROFILES"
LOCATE 6,24:PRINT "---- ------------ --------"
FOR J=0 TO 50
    IF TLABEL$(J)="MALOTT" THEN 1110
    LOCATE J+8,5:PRINT J+1
    LOCATE J+8,10:PRINT TLABEL$(J)
NEXT J
FOR J=0 TO 50
    IF TLABEL$(J)="MALOTT" THEN 121
    LOCATE J+8,35:PRINT USING "###.#";TV(J)
NEXT J

'***********************
'    Comment Profiles
'***********************
CLS:LOCATE 3,28:PRINT "COMMENT PROFILES"
LOCATE 4,28:PRINT "------- --------"
FOR L=1 TO 50
    IF COMMENT$(L)="HALF LIFE" THEN 1250
    LOCATE L+6,10:PRINT L
    LOCATE L+6,20:PRINT COMMENT$(L)
NEXT L ON ERROR GOTO 1500
LOCATE 23,10:INPUT "ENTER THE COMMENT YOU WISH TO MAKE:";NV
IF COMMENT$(NV)="CANCEL COMMENT" THEN 600
CMMT$=COMMENT$(NV)
IF COMMENT$(NV)="INPUT COMMENT" THEN
    LOCATE 18,15:INPUT "ENTER YOUR COMMENT:";CMMT$
END IF
TRIP=30:GOTO 600

'***********************
'    Shut Down Variables
'***********************
TSP=0:TOSP=0:SEP=1:WAS=1
ASP=0:WSP=2.5
TEMPSP=30
TVA!=0:TOVA!=0
AVA!=0:WVA!=0:SEPVAR=3900:WASHVAR=3900
LEVELCNTRL!=SEPVAR:WASHCNTRL!=WASHVAR
CMMT$="SHUT DOWN":TRIP=30:SHUT=1:GOTO 600

'***********************
'    Start Up Variables
'***********************
TSP=SP*D/100/(B-C*D/100)
ASP=TSP*CH*17/35.454/100/.28
WSP=SP*1.1/2
TOSP=SP:SEP=0:WAS=0
KLEVEL=18:KWASH=10:SEPVAR=1900:WASHVAR=3900
CMMT$="START UP":TRIP=30:SHUT=0:GOTO 600

'***********************
'    Error Trap
'***********************
```

```
IF (ERR=5) THEN RESUME 110
IF (ERR=11) THEN RESUME 10
RESUME NEXT

'***************************
'   Manual Sep Control
'***************************
CALL MEANDEV("SEPIN%",1,GV(6),STDEV,1.0,15.0,0)
CV(6)=GV(6)
IF GV(6)<.80 THEN GV(6)=0
LEVELCNTRL!=KLEVEL/100*3900
IF LEVELCNTRL!<0 THEN LEVELCNTRL!=0
IF LEVELCNTRL!>3900 THEN LEVELCNTRL!=3900
PERLEVEL=KLEVEL
GOTO 106

'***************************
'   Manual Wash Control
'***************************
CALL MEANDEV("WASHIN%",1,GV(7),STDEV,1.0,5.0,0)
CV(7)=GV(7)
IF GV(7)<.88 THEN GV(7)=0
WASHCNTRL!=KWASH/100*3900
IF WASHCNTRL!<0 THEN WASHCNTRL!=0
IF WASHCNTRL!>3900 THEN WASHCNTRL!=3900
PERWASH=KWASH
GOTO 107

'***************************
'  Manual Control Screen
'***************************
CLS:LOCATE 4,32:PRINT "MANUAL CONTROLS"
LOCATE 5,32:PRINT "------ --------"
FOR M=1 TO 50
   IF MANUAL$(M)="HALF LIFE" THEN  1850
   LOCATE M+6,10:PRINT M
   LOCATE M+6,20:PRINT MANUAL$(M)
NEXT M
LOCATE 20,10:INPUT "ENTER THE VARIABLE YOU WISH:";NV
IF MANUAL$(NV)="CANCEL" THEN 600
IF MANUAL$(NV)="MANUAL SEP" THEN
   SEP=1:KLEVEL=PERLEVEL
   LOCATE 16,15:PRINT "KLEVEL?";KLEVEL
   LOCATE 16,21:INPUT KLEVEL
   GOTO 600
END IF
IF MANUAL$(NV)="AUTOMATIC SEP" THEN
   SEP=0:KLEVEL=18
END IF
IF MANUAL$(NV)="MANUAL WASH" THEN
   WAS=1:KWASH=PERWASH
   LOCATE 17,15:PRINT "KWASH?";KWASH
   LOCATE 17,20:INPUT KWASH
   GOTO 600
END IF
IF MANUAL$(NV)="AUTOMATIC WASH" THEN
   WAS=0:KWASH=10
END IF
IF MANUAL$(NV)="ALL MANUAL" THEN
   SEP=1:WAS=1
```

```
    KWASH=PERWASH:KLEVEL=PERLEVEL
    LOCATE 16,15:PRINT "KLEVEL?";KLEVEL
    LOCATE 16,21:INPUT KLEVEL
    LOCATE 17,15:PRINT "KWASH?";KWASH
    LOCATE 17,20:INPUT KWASH
    GOTO 600
END IF
IF MANUALS(NV)="ALL AUTOMATIC" THEN
    SEP=0:WAS=0
END IF
GOTO 600
```

It will be apparent to one of ordinary skill that although it is much more economical to operate the method of this invention in but one agitated vessel as described hereinabove and in the following examples, there is no reason why the vigorous agitation of the reaction mixture could not be conducted in a series of agitated vessels before separation is commenced. Thus, the operation of this method with its essential agitation, as defined herein, in more than one agitated vessel is considered equivalent to its operation in but one.

EXAMPLE 1

Twenty-seven hundred grams of water were placed in a 3 liter reactor having a diameter of 5" and equipped with a center-mounted laboratory style mixer having two 2.5"-inch diameter LIGHTNIN A310 impellers spaced 4 inches apart on the mixer shaft. The mixing was started at a shaft speed of about 1300 RPM and the addition of a 50% by weight aqueous solution of alkyltin chloride (80% dimethyltin dichloride, 20% monomethyltin trichloride by weight) at 210 grams/minute, 2-ethylhexylthioglycolate at 213 grams/minute, water at 107 grams per minute, and concentrated ammonium hydroxide (28% by weight) was started. The two organic reactants were added continuously in essentially stoichiometric proportions as controlled by a computer, but the addition of the ammonium hydroxide was controlled by the computer to maintain a constant pH of 8.2. About 60 grams/minute of the acid acceptor was added during the course of the continuous preparation of the alkyltin 2-ethylhexylthioglycolate, which was continued for about 5 hours. The liquid level in the reactor was 8 inches; the operating volume was, therefore, 2.575 liters (0.68 gallon) and the Z-factor was 1.6. At this mixer speed, the turnover rate was about 130 per minute and the average bulk fluid velocity was about 88 feet/minute. The additions and a continuous withdrawal of the reaction mixture into a gravity settling separation unit were commenced simultaneously at the same rate. The mixture separated quickly and the organic phase was washed with water and dried by heating under vacuum. The residence time in the stirred reaction vessel was about 4.5 minutes. A sample of the dried product had a tin content of 18.8% by Refractive Index measurement, 18.96% by atomic absorption spectra, and 18.6% by X-ray analysis. The theoretical content of tin in the product, taking into account the amounts of ester and alkyltin chloride charged and the concentrations of dimethyltin and monomethyltin chlorides therein, is 18.9% by weight.

EXAMPLE 2

A five-gallon, baffled cylindrical reactor vessel, having a diameter of 11.5 inches was charged with 33 pounds of water and agitation was started with a top-entering center-mounted LIGHTNIN Series XDQ, Model XDQ-75SCR mixer equipped with dual A310 laser foil impellers having a 5.2 inch diameter and spaced 4 inches apart. Said mixer has a 0.75 HP, variable speed (1750 RPM max), DC motor. The pumping rate of the impellers was 1013 gallons per minute and the fluid velocity across the impellers was 188 feet per minute. The simultaneous addition of the aqueous solution of the mixture of dimethyltin dichloride and monomethyltin trichloride (like that in Example 1), the 2-ethylhexylthioglycolate, water, and the ammonium hydroxide was then started. The rates of addition of the organic reactants were: 2.67 pounds per minute of the alkyltin chloride, 1.36 pounds per minute of water, and 2.7 pounds per minute of the thioglycolate. The ammonium hydroxide was added at a rate sufficient to maintain the pH at 8.2 (about 1 pound per minute). The additions were continued for 109 minutes and the temperature was maintained at 45° C. Withdrawal of the reaction mixture at a rate equal to the combined addition rates commenced as the mixture overflowed from the reactor and the mixture was continuously led into a separation tank where the aqueous phase separated quickly and cleanly from the organic phase. Said aqueous phase contained only 360 ppm of tin - an indication of the completeness of the desired reaction and lack of side reactions. The product phase was washed with fresh water and dried with heat and vacuum. The percent tin in the dry product was 18.8 by the refractive index method, 18.9 by the X-ray method, and 18.83 by density.

The following examples illustrate the criticality of the turnover rate in achieving continuous manufacture of the ester.

EXAMPLE 3

The general procedure of Example 1 was followed except that the residence time was 5 minutes and the speed of the impellers was varied from a high of about 1300 rpm to a low of about 800 rpm. Separation of the emulsion created by the agitation was substantially instantaneous and complete at a speed as low as 910 rpm but it was unsatisfactorily slow at a speed of 800 rpm. At this low impeller speed, the pumping rate of the impellers was about 55 gallons per minute and the turnover rate was about 81. At an impeller speed of 910 rpm, the pumping rate was about 63 gallons per minute and the turnover rate was about 93.

EXAMPLE 4

The general procedure of Example 1 was followed except that the residence time was about 3.6 minutes and the impeller speed was varied from about 1300 rpm to a low of 910 rpm. The separation of the emulsion was substantially instantaneous and complete at 1145 rpm but it was unsatisfactory at 910 rpm.

The subject matter claimed is:

1. A method for the continuous manufacture of an alkyltin thiocarboxylic acid ester comprising simultaneously adding an alkyltin halide, a thiocarboxylic acid ester, and an acid acceptor to an agitated aqueous medium in a reaction vessel over an indefinite period of time, agitating the mixture with one or more impellers at a turnover per minute rate of at least about 90 substantially throughout the volume of the mixture, maintaining the resulting reaction mixture at a pH of from greater than 7 to about 8.2, continuously withdrawing the mixture from said reaction vessel simultaneously with the addition of the reactants, and continuously separating it as it is withdrawn into an aqueous phase and an organic phase without the need for demulsification means.

2. The method of claim 1 wherein the turnover rate is at least about 110 per minute.

3. The method of claim 1 wherein the pH is from about 8 to about 8.2.

4. The method of claim 1 wherein the turnover rate is at least about 120.

5. The method of claim 1 wherein the alkyltin halide, the ester, and the acid acceptor are added beneath the surface of the liquid in the reaction vessel.

6. The method of claim 1 wherein the alkyltin thiocarboxylic ester has the structure:

$$R_xSn[S(CH_2)_n(COOR']_{4-x}$$

wherein x is 1 or 2, and n is 1 or 2; R is an alkyl group having from one to four carbon atoms; and R' is an alkyl group having from eight to sixteen carbon atoms.

7. The method of claim 6 wherein R is methyl.

8. The method of claim 6 wherein R' is 2-ethylhexyl.

9. The method of claim 7 wherein R' is 2-ethylhexyl.

* * * * *